US012808001B2

(12) United States Patent
Krogerus et al.

(10) Patent No.: US 12,808,001 B2
(45) Date of Patent: Nov. 24, 2026

(54) METHOD FOR DETERMINING A YEAST HAVING EXTRACELLULAR GLUCOAMYLASE STAIP ACTIVITY IN A SAMPLE AND TOOLS AND USES RELATED THERETO

(71) Applicant: TEKNOLOGIAN TUTKIMUSKESKUS VTT OY, Espoo (FI)

(72) Inventors: Kristoffer Krogerus, Vtt (FI); Brian Gibson, Vtt (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 1139 days.

(21) Appl. No.: 17/615,271

(22) PCT Filed: May 29, 2020

(86) PCT No.: PCT/FI2020/050360
§ 371 (c)(1),
(2) Date: Nov. 30, 2021

(87) PCT Pub. No.: WO2020/240091
PCT Pub. Date: Dec. 30, 2020

(65) Prior Publication Data

US 2022/0235424 A1 Jul. 28, 2022

(30) Foreign Application Priority Data

May 31, 2019 (FI) ..................................... 20195454

(51) Int. Cl.
*C12Q 1/6895* (2018.01)

(52) U.S. Cl.
CPC ..... *C12Q 1/6895* (2013.01); *C12Q 2600/156* (2013.01)

(58) Field of Classification Search
CPC ......... C12Q 1/68; C12Q 1/6876; C12Q 1/686
See application file for complete search history.

(56) References Cited

U.S. PATENT DOCUMENTS

| | | | |
|---|---|---|---|
| 6,303,302 | B1 | 10/2001 | Rupp et al. |
| 2006/0046253 | A1 | 3/2006 | Nakao et al. |
| 2007/0118916 | A1 | 5/2007 | Puzio et al. |

FOREIGN PATENT DOCUMENTS

| | | | |
|---|---|---|---|
| JP | 4037926 | B2 | 1/2008 |
| JP | 2011223940 | A | 11/2011 |
| WO | 2011132667 | | 10/2011 |

OTHER PUBLICATIONS

Shima et al. (1989). Upstream Regions of the Yeast Glucoamylase Gene Which Are Required for Efficient Transcription. Agricultural and Biological Chemistry, 53(3), 749-755. doi.org/10.1080/00021369.1989.10869353; cited as NPL#25 in IDS filed on Nov. 30, 2021 (Year: 1989).*

Kim et al. Glucose repression of STA1 expression is mediated by the Nrgl and Sfl1 repressors and the Srb8-11 complex. Mol Cell Biol. Sep. 2004;24(17):7695-706. doi: 10.1128/MCB.24.17.7695-7706.2004. PMID: 15314176; PMCID: PMC507009; cited as NPL #15 in IDS filed on Nov. 30, 2021 (Year: 2004).*

Meier-Dornberg et al. *Saccharomyces cerevisiae* variety diastaticus friend or foe? FEMS Yeast Res. Jun. 1, 2018;18(4). doi: 10.1093/femsyr/foy023. PMID: 29518233. cited as NPL#20 in IDS filed on Nov. 30, 2021 (Year: 2018).*

Mitro, A. (Oct. 16, 2018). Demystifying diastaticus (part 1). Escarpment Labs.; escarpmentlabs.com/en-us/blogs/resources/demystifying-diastaticus-part-1 (Year: 2018).*

Shima et al. (1989). Upstream Regions of the Yeast Glucoamylase Gene Which Are Required for Efficient Transcription. Agricultural and Biological Chemistry, 53(3), 749-755 (Year: 1989).*

Meier-Dornberg et al. *Saccharomyces cerevisiae* variety diastaticus friend or foe? FEMS Yeast Res. Jun. 1, 2018;18(4). doi: 10.1093/femsyr/foy023. PMID: 29518233 (Year: 2018).*

Salinas et al. Natural variation in non-coding regions underlying phenotypic diversity in budding yeast. Sci Rep 6, 21849 (Year: 2016).*

Steensels et al. Improving industrial yeast strains: exploiting natural and artificial diversity. FEMS Microbiol Rev. Sep. 2014;38(5): 947-95. doi: 10.1111/1574-6976.12073. Epub May 8, 2014. PMID: 24724938; PMCID: PMC4293462 (Year: 2014).*

(Continued)

*Primary Examiner* — Aaron A Priest
*Assistant Examiner* — Tian Yu
(74) *Attorney, Agent, or Firm* — Meunier Carlin & Curfman LLC

(57) ABSTRACT

The present invention relates to the fields of genetic testing and furthermore determining specific yeasts. Specifically, the invention relates to a method for determining a yeast having extracellular glucoamylase STA1 p activity in a sample, a primer capable of hybridizing with STA1 gene of a yeast, a primer pair comprising two primers capable of hybridizing with STA1 gene of a yeast, and a probe capable of hybridizing with the promoter of STA1 gene of a yeast e.g. within a very specific region. Also, the present invention relates to a kit for genetic testing. And still, the present invention relates to use of the primer, primer pair, probe or kit of the present invention for detecting the presence or absence of a deletion in the promoter of STA1 gene in a yeast.

11 Claims, 3 Drawing Sheets

Specification includes a Sequence Listing.

(56) References Cited

OTHER PUBLICATIONS

Metzger et al. Contrasting Frequencies and Effects of cis- and trans-Regulatory Mutations Affecting Gene Expression, Molecular Biology and Evolution, vol. 33, Issue 5, May 2016, pp. 1131-1146 (Year: 2016).*

International Search Report and Written Opinion issued for Application No. PCT/FI2020/050360, dated Jul. 23, 2020.

Search Report issued for Finnish Application No. 20195454, dated Nov. 12, 2019. 2 pages.

"Annex 1(sequence alignments)" In:"Annex 1(sequence alignments)", Jul. 14, 2020 (Jul. 14, 2020. pp. 1-2. XP055714636.

Bajszár, George, et al. "Properties and Engineering of a Mutant STA Promoter of *Saccharomyces diastaticus*." Applied biochemistry and biotechnology 44.2 (1994): 187-204. XP035176924.

Brandl, A., 2006, PhD thesis, Entwicklung und Optimierung von PCR-Methoden zur Detektion und Identifizierung von brauereirelevanten Mikroorganismen zur Routine-Anwendung in Brauereien, 179 pages, Technische Universität München. English Abstract included.

Gietz, R. Daniel, and Robin A. Woods. "Transformation of yeast by lithium acetate/single-stranded carrier DNA/polyethylene glycol method." Methods in enzymology 350 (2002): 87-96.

Kim, Keun, et al. "Cloning of a new allelic variant of a *Saccharomyces diastaticus* glucoamylase gene and its introduction into industrial yeasts." Applied biochemistry and biotechnology 44.2 (1994): 161-185. XP035176922.

Kim, Tae Soo, et al. "Recruitment of the Swi/Snf complex by Ste12-Tecl promotes Flo8-Mss11-mediated activation of STA1 expression." Molecular and cellular biology 24.21 (2004): 9542-9556.

Kim, Tae Soo, Sung Bae Lee, and Hyen Sam Kang. "Glucose repression of STA1 expression is mediated by the Nrgl and Sfll repressors and the Srb8-11 complex." Molecular and cellular biology 24.17 (2004): 7695-7706.

Kleinman, M. J., et al. "Purification and properties of an extracellular glucoamylase from a diastatic strain of *Saccharomyces cerevisiae*." Biochemical journal 249.1 (1988): 163-170.

Krogerus, Kristoffer, and Brian Gibson. "A re-evaluation of diastatic *Saccharomyces cerevisiae* strains and their role in brewing." Applied microbiology and biotechnology 104.9 (2020): 3745-3756. XP037093516.

Krogerus, Kristoffer, et al. "A deletion in the STA1 promoter determines maltotriose and starch utilization in STA1+ *Saccharomyces cerevisiae* strains." Applied microbiology and biotechnology 103.18 (2019): 7597-7615. XP036875349.

Lambrechts, Marius G., et al. "Primary structure and regulation of a glucoamylase-encoding gene (STA2) in *Saccharomyces diastaticus*." Gene 100 (1991): 95-103.

Meier-Dörnberg, Tim, et al. "*Saccharomyces cerevisiae* variety diastaticus friend or foe?—spoilage potential and brewing ability of different *Saccharomyces cerevisiae* variety diastaticus yeast isolates by genetic, phenotypic and physiological characterization." FEMS yeast research 18.4 (2018): foy023.

Pfaffl, Michael W. "A new mathematical model for relative quantification in real-time RT-PCR." Nucleic acids research 29.9 (2001): e45.

Pretorius, Isak S., et al. "Transcriptional control of glucoamylase synthesis in vegetatively growing and sporulating *Saccharomyces species*." Molecular and cellular biology 6.9 (1986): 3034-3041.

Rantasalo, Anssi, et al. "Synthetic toolkit for complex genetic circuit engineering in *Saccharomyces cerevisiae*." ACS synthetic biology 7.6 (2018): 1573-1587.

Shedlovskiy, Daniel, Natalia Shcherbik, and Dimitri G. Pestov. "One-step hot formamide extraction of RNA from *Saccharomyces cerevisiae*." RNA biology 14.12 (2017): 1722-1726.

Shima, H et al. "Upstream regions of the yeast glucoamylase gene which are required for efficient transcription." In: Agricultural and Biological Chemistry 1989, vol. 53, No. 3, pp. 749-755.

Stemmer, Manuel, et al. "CCTop: an intuitive, flexible and reliable CRISPR/Cas9 target prediction tool." PloS one 10.4 (2015): e0124633. Apr. 20, 2017: Stemmer M, Thumberger T, del Sol Keyer M, Wittbrodt J, Mateo JL (2017) Correction: CCTop: An Intuitive, Flexible and Reliable CRISPR/Cas9 Target Prediction Tool. PLOS One 12(4): e0176619. https://doi.org/10.1371/journal.pone.0176619.

Tamaki, Hideo. "Genetic studies of ability to ferment starch in *Saccharomyces*: gene polymorphism." Molecular and General Genetics MGG 164.2 (1978): 205-209.

Teste, Marie-Ange, et al. "Validation of reference genes for quantitative expression analysis by real-time RT-PCR in *Saccharomyces cerevisiae*." BMC molecular biology 10.1 (2009): 99.

Van der Aa Kühle, A., and L. Jespersen. "Detection and identification of wild yeasts in lager breweries." International journal of food microbiology 43.3 (1998): 205-213.

Yamashita, et al. "Polymorphic extracellular glucoamylase genes and their evolutionary origin in the yeast *Saccharomyces diastaticus*." Journal of bacteriology 161.2 (1985): 574-582.

Yamashita, et al., "Nucleotide sequence of the extracellular glucoamylase gene STA1 in the yeast *Saccharomyces diastaticus*." Journal of bacteriology 161.2 (1985): 567-573.

Yamauchi, Hiromasa, et al. "Rapid methods for detecting *Saccharomyces diastaticus*, a beer spoilage yeast, using the polymerase chain reaction." Journal of the American Society of Brewing Chemists 56.2 (1998): 58-63. XP055714514.

* cited by examiner

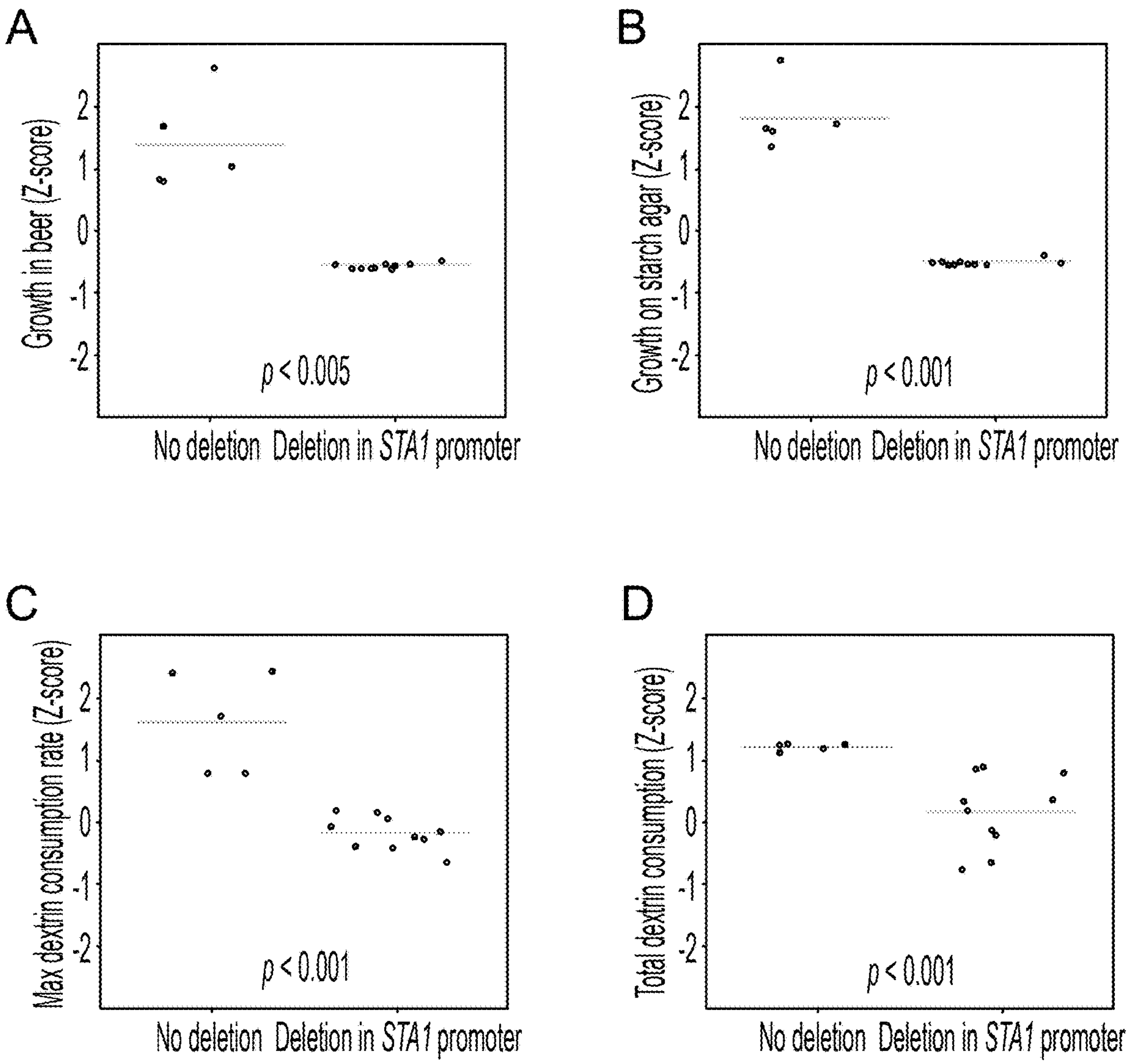
Figures 1A-D.

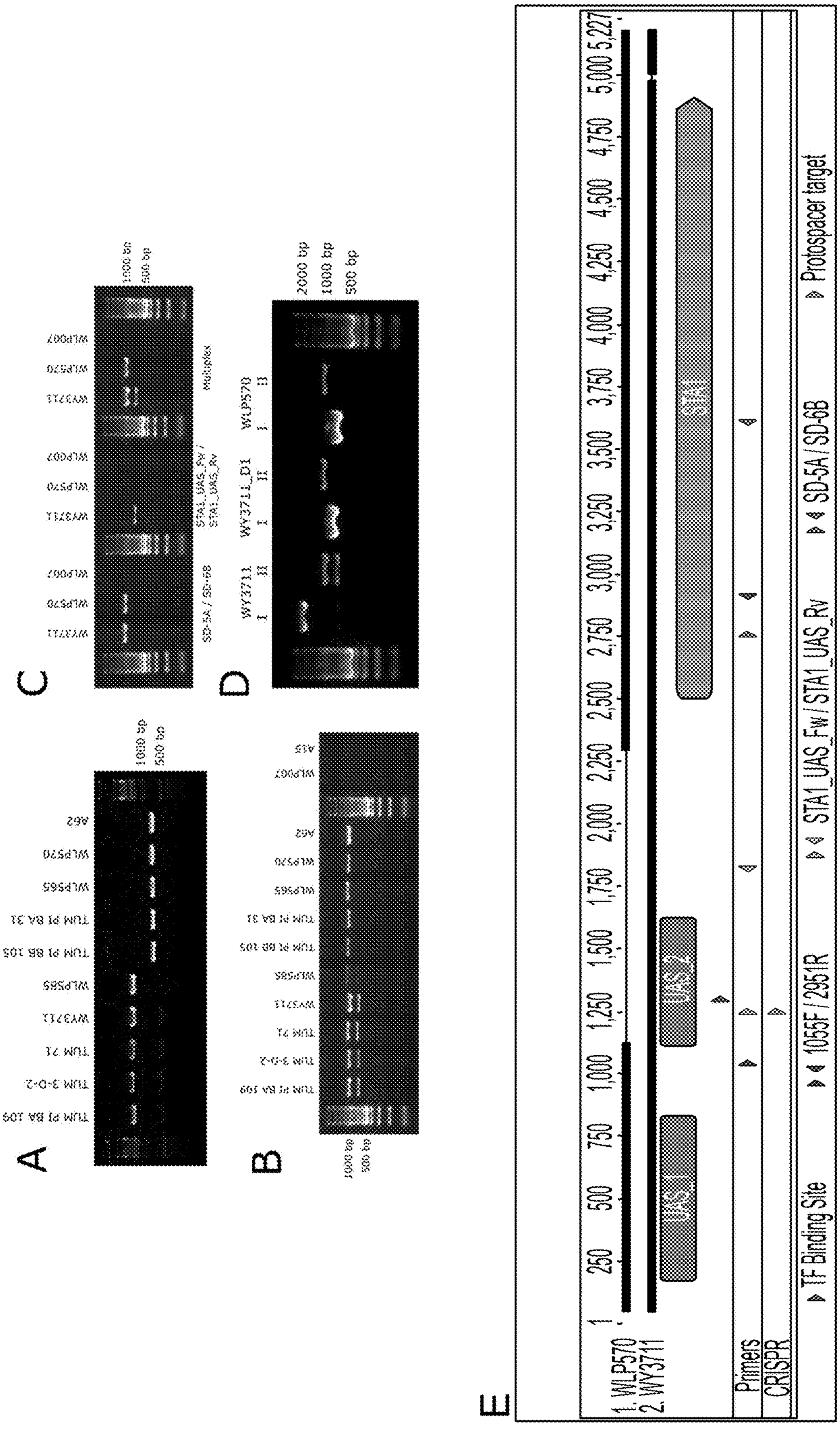
Figures 2A-E.

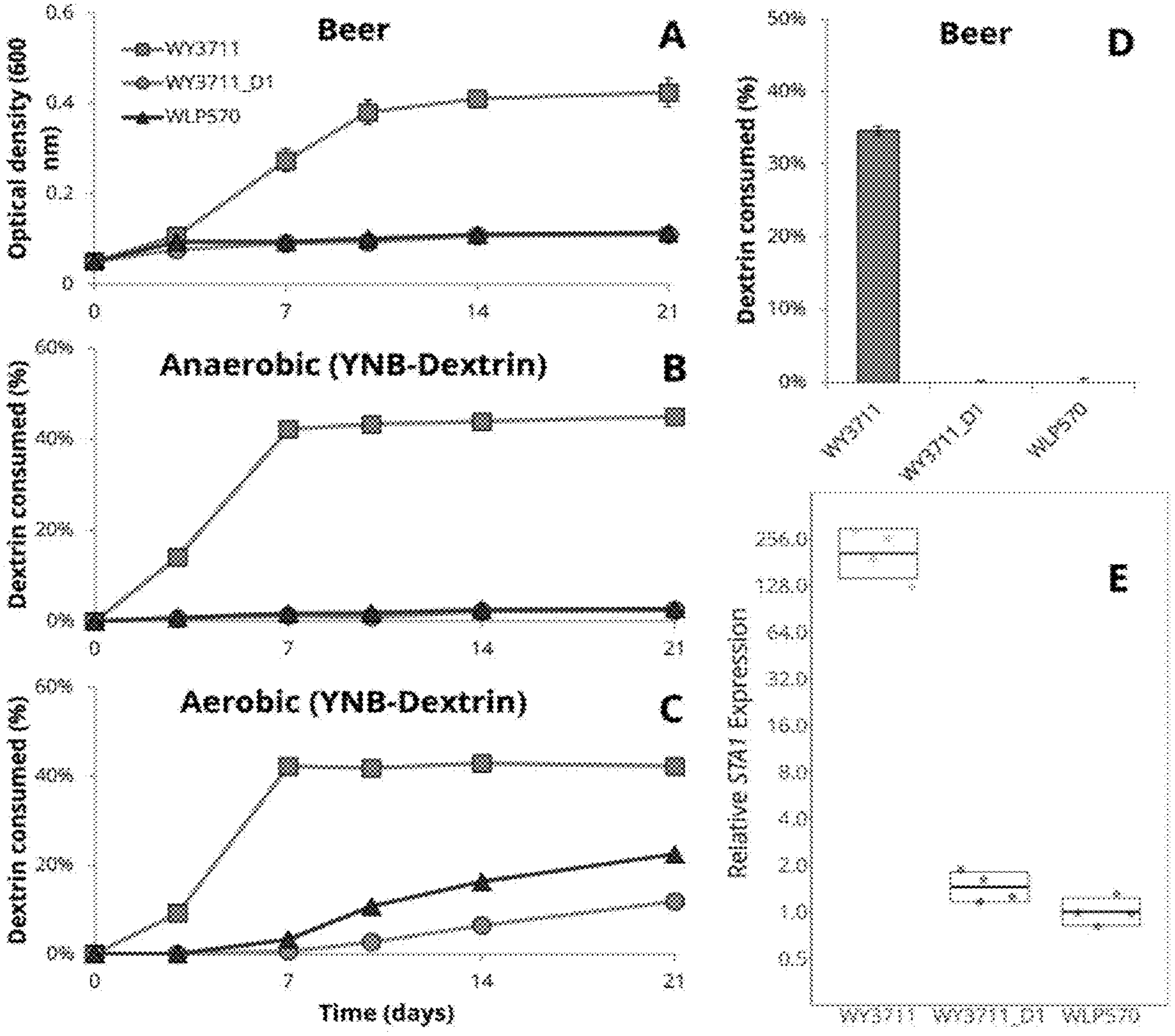
Figures 3A-E.

METHOD FOR DETERMINING A YEAST HAVING EXTRACELLULAR GLUCOAMYLASE STAIP ACTIVITY IN A SAMPLE AND TOOLS AND USES RELATED THERETO

CROSS REFERENCE TO RELATED APPLICATIONS

This application is a United States National Phase Patent Application of International Patent Application Number PCT/FI2020/050360, filed on May 29, 2020, claiming priority of Finnish national application number FI20195454 filed on May 31, 2019, both of which are incorporated by reference herein in their entirety.

REFERENCE TO SEQUENCE LISTING

A Sequence Listing conforming to the rules of WIPO Standard ST.25 is hereby incorporated by reference. Said Sequence Listing has been filed as an electronic document via PatentCenter as UTF-8 text. The electronic document, created on Aug. 4, 2026, is entitled "MCC-338-WO-S25_ST25.txt", and is 14,492 bytes in size.

FIELD OF THE INVENTION

The present invention relates to the fields of genetic testing and furthermore determining specific yeasts. Specifically, the invention relates to a method for determining a yeast having extracellular glucoamylase STA1p activity in a sample, a primer capable of hybridizing with STA1 gene of a yeast, a primer pair comprising two primers capable of hybridizing with STA1 gene of a yeast, and a probe capable of hybridizing with the promoter of STA1 gene of a yeast e.g. within a very specific region. Also, the present invention relates to a kit for genetic testing. And still, the present invention relates to use of the primer, primer pair, probe or kit of the present invention for detecting the presence or absence of a deletion in the promoter of STA1 gene in a yeast.

BACKGROUND OF THE INVENTION

Some diastatic strains of yeast are considered spoilage microorganisms in industrial lager fermentations. These strains, including but not limited to *Saccharomyces cerevisiae* formerly known as *Saccharomyces diastaticus*, are capable of producing an extracellular glucoamylase that enables fermentation of starch and oligosaccharides. This in turn, causes super-attenuation in the beer, which leads to increased carbon dioxide and ethanol levels, possible off-flavours, and a drier mouthfeel. In the case of contamination in packaged beer, diastatic *S. cerevisiae* may even cause exploding bottles and cans, endangering the consumer.

The extracellular glucoamylase in diastatic *S. cerevisiae* is coded for by the STA genes (Tamaki, 1978, *MGG Mol. Gen. Genet*. Volume 164, issue 2, 205-209; Yamashita et al., 1985, *J. Bacteriol.* 161, 574-582; Yamashita, et al., 1985, *J. Bacteriol.* 161, 567-573). Three highly homologous STA genes (STA1-3) have been described (Tamaki, 1978, *MGG Mol. Gen. Genet*. Volume 164, issue 2, 205-209; Lambrechts et al. 1991, *Gene*, vol. 100, 95-103). STA1p is the main cause of spoilage features in said *S. cerevisiae*. Genetic differentiation of spoilage and non-spoilage yeast strains is important e.g. for the food industry in order to minimize the production costs and optimize the quality of end products.

Current detection methods for diastatic *S. cerevisiae* rely mainly on either the microbiological detection through culturing on specialized selective growth media, or the molecular detection of the STA1 gene through conventional or quantitative PCR (Brandl, A., 2006, PhD thesis, Entwicklung und Optimierung von PCR-Methoden zur Detektion und Identifizierung von brauereirelevanten Mikroorganismen zur Routine-Anwendung in Brauereien, 179 pages, Technische Universität München); Meier-Dörnberg et al., 2018, *FEMS Yeast Res.* 18, issue 4, foy023; Van Der Aa Kühle and Jespersen, 1998, *Int. J. Food Microbiol.* 43(3): 205-213; Yamauchi et al., 1998, *J. Am. Soc. Brew. Chem.* 56, 58-63).

The main weakness of the microbiological methods is that they are time-consuming and thus expensive. While the current molecular methods are rapid, they are not able to determine all those yeast strains that do not show spoilage potential. Therefore, with the current genetic tests these benign strains would be erroneously flagged as diastatic and needlessly removed. For example breweries might unnecessarily be recalling and discarding beer that has been erroneously flagged as containing diastatic yeast based on the prior art genetic tests. One example of said unreliable prior art genetic tests has been described in JP2011223940 defining a PCR based method for detecting specific microorganisms, wherein in one embodiment said method comprises detecting a target gene STA1 in *S. cerevisiae.*

Indeed, there remains a significant unmet and long-felt need for a method and tools for specifically detecting only those yeasts, which are diastatic, or on the other hand determining exactly those yeasts, which are non-diastatic.

BRIEF DESCRIPTION OF THE INVENTION

There is considerable variability in diastatic ability and beer-spoilage potential in yeast strains carrying the STA1 gene. Now, the present invention provides a method, which is able to detect non-spoilage and spoilage yeast strains very reliably, also among those yeasts which carry a STA1 gene. More specifically the present invention is based on the surprising finding that non-spoilage yeast strains carrying the STA1 gene have a specific alteration in said STA1 gene. Therefore, the objects of the invention, including but not limited to obtaining specific genetic methods and tools for differentiating spoilage and non-spoilage yeast strains, are achieved by utilizing the specific region of the STA1 gene.

The present invention overcomes the defects and problems of the prior art including lack of methods for determining yeast strains that carry the STA1 gene but do not show spoilage potential. Indeed, the number of false diastatic positives among yeast strains can be greatly reduced with the method and tools presented herein. The genetic method of the present invention is cheap and fast enabling the results in hours instead of days. Also, the method and tools of the present invention enable lowered production costs and effective large-scale production processes of food and beverages, because based on the present invention only the specific non-diastatic yeast strains can be utilized in said processes. Indeed, optimizing use of suitable, i.e. non-diastatic, yeast strains e.g. in food industry is possible with the present invention and therefore, unnecessary economic losses can be avoided.

More specifically it has now been surprisingly found that the poorly diastatic yeasts have a specific deletion in the promoter or upstream region of STA1 gene. Said deletion greatly decreases diastatic ability and the expression of STA1. A specific object of the present invention is thus to provide tools and a method for effectively differentiating highly and poorly diastatic yeasts by utilizing the specific region of the STA1 gene shown to be deleted in poorly diastatic yeasts.

The present invention relates to a method for determining a yeast having extracellular glucoamylase STA1p activity in a sample, wherein the method comprises detecting the presence or absence of a deletion in the promoter of STA1 gene in a sample. The present invention also relates to a method for determining a yeast having extracellular glucoamylase STA1p activity in a sample, wherein the method comprises allowing a primer or probe capable of hybridizing with the promoter of STA1 gene (e.g. within or partly within nucleotides 1127-2288 as numbered in SEQ ID NO: 1) to hybridize with a polynucleotide of the sample, and detecting the presence or absence of a deletion in the promoter of STA1 gene in a sample.

Also, the present invention relates to a primer capable of hybridizing with STA1 gene of a yeast (optionally for determining a yeast having extracellular glucoamylase STA1p activity or for detecting the presence or absence of a deletion in the promoter of STA1 gene), wherein said primer is capable of hybridizing with the promoter of STA1 gene within nucleotides 1127-2288 as numbered in SEQ ID NO: 1.

Also, the present invention relates to a primer pair (optionally for determining a yeast having extracellular glucoamylase STA1p activity or for detecting the presence or absence of a deletion in the promoter of STA1 gene) comprising two primers capable of hybridizing with STA1 gene of a yeast, wherein at least one of said primers is capable of hybridizing with the promoter of STA1 gene within nucleotides 1127-2288 as numbered in SEQ ID NO: 1.

Still, the present invention relates to a probe capable of hybridizing with the promoter of STA1 gene of a yeast within or at least partially within nucleotides 1127-2288 as numbered in SEQ ID NO: 1 (optionally for determining a yeast having extracellular glucoamylase STA1p activity or for detecting the presence or absence of a deletion in the promoter of STA1 gene).

And still, the present invention relates to a kit for genetic testing comprising a primer, primer pair or probe of the present invention and optionally reagents for performing said genetic testing.

Still furthermore, the present invention relates to use of the primer, primer pair, probe or kit of the present invention for detecting the presence or absence of a deletion in the promoter of STA1 gene in a yeast.

And still furthermore, the present invention relates to a (genetically) modified yeast comprising a deletion in the promoter of STA1 gene, e.g. said deletion comprising or being within nucleotides 1127-2288 as numbered in SEQ ID NO: 1.

Other objects, details and advantages of the present invention will become apparent from the following drawings, detailed description and examples.

BRIEF DESCRIPTION OF THE DRAWINGS

FIGS. 1A-D show the results of screening the diastatic ability. Diastatic assays show that despite carrying the STA1 gene, only five out of 15 strains were able to grow in beer and on starch agar (FIG. 1). The strains with the deletion in the promoter of STA1 gene exhibited significantly less diastatic ability in all tests (FIG. 1A: growth in beer; FIG. 1B: growth on starch agar; FIGS. 1C-D: fermentation of dextrin) between STA1+ strains with no deletion in the STA1 promoter compared to strains with a deletion in the STA1 promoter. The statistical significance between the two groups was tested with the Mann-Whitney U test.

FIGS. 2A-E reveal a specific deletion in the promoter of STA1 gene. A 1162 bp deletion was shown upstream of STA1 (−1370 to −209 from the start codon), i.e. in the promoter of STA1 gene, in 10 out of the 15 yeast strains (FIG. 2A). To improve the reliability of the molecular detection methods for diastatic *S. cerevisiae*, two new primer pairs were designed to bind within the 1162 bp region that is absent in the poorly diastatic STA1+ strains. These new primers can therefore be 25 used to differentiate whether a strain that has tested positive for STA1 with the SD-5A/SD-6B primers (Yamauchi et al. 1998) is likely to be highly diastatic or not. The first primer pair (STA1_UAS_Fw/STA1_UAS_Rv) was designed to produce a 599 bp amplicon, and can be used together with the SD-5A/SD-6B primers in a single multiplex PCR reaction (FIGS. 2B-C). To confirm that the 1162 bp deletion that was observed in the STA1 promoter had a negative effect on diastatic ability and STA1 expression, we performed reverse engineering aided by the CRISPR/Cas9 system. The gRNA protospacer sequence was designed to cause a: double-stranded break within the region to be deleted (FIG. 2E). The 1162 bp region (−1370 to −209 upstream of the STA1 open reading frame) was deleted from the highly diastatic WY3711 strain by transformation with a Cas9- and gRNA-expressing plasmid and an 80 bp double-stranded repair oligo. PCR using primer pairs binding within (STA1_UAS_Fw/STA1_UAS_Rv) and outside the deleted region (1055F/2951R) was used to confirm successful deletion (FIG. 2D).

FIGS. 3A-E show phenotypic results of the reverse engineered strain, WY3711_D1. Three STA1+ strains were compared: WY3711 (no deletion in STA1 promoter), WY3711_D1 (CRISPR-mediated deletion in STA1 promoter), and WLP570 (natural deletion in STA1 promoter). (FIG. 3A) The optical density (600 nm) when strains were inoculated into beer at a starting value of 0.1. Values for WY3711 were different from the two other strains starting from day 7 ($p<0.01$ by two-tailed Student's t-test). (FIGS. 3B-C) The amount of dextrin consumed from YNB-Dextrin media in anaerobic (3B) and aerobic (3C) conditions. Values for WY3711 were different from the two other strains starting from day 4 ($p<0.01$ by two-tailed Student's t-test). (FIG. 3D) The amount of dextrin consumed from the beer (3A) after 3 weeks of incubation. (FIG. 3E) The relative expression of STA1 (normalized to ALG9 and UBC6) determined by RT-qPCR in derepressed conditions. Points indicate values from four biological replicates and boxes indicate the mean and standard deviation. Values for WY3711 were significantly higher than those of the two other strains ($p<0.01$ by two-tailed Student's t-test).

SEQUENCE LISTING

SEQ ID NO:1: nucleotide sequence of STA1 (*S. cerevisiae*) promoter and open reading frame, wherein a deletion may comprise or a deletion may be within nucleotides 1127-2288

SEQ ID NO: 2 oligonucleotide, primer used for the detection of intact STA1 promoter, STA1_UAS_Fw SEQ ID NO: 3 oligonucleotide, primer used for the detection of intact STA1 promoter, STA1_UAS_Rv SEQ ID NO: 4 oligonucleotide, primer used for the detection of intact STA1 promoter, STA1_UAS_Q_Fw SEQ ID NO: 5 oligonucleotide, primer used for the detection of STA1, SD-5A SEQ ID NO: 6 oligonucleotide, primer used for the detection of STA1, SD-6B SEQ ID NO: 7 oligonucleotide, primer used for amplification and sequencing of STA1, STA1_Full_Fw SEQ ID NO: 8 oligonucleotide, primer used for amplification and sequencing of STA1, STA1_Full_Rv SEQ ID NO: 9 oligonucleotide, primer used for amplification and sequencing of STA1, STA1_24_F SEQ ID NO: 10 oligonucleotide, primer used for amplification and sequencing of STA1, STA1_546_R SEQ ID NO: 11 oligonucleotide, primer used for amplification and sequencing of STA1, STA1_482_F SEQ ID NO: 12 oligonucleotide, primer used for amplification and sequencing of STA1, STA1_1148_R SEQ ID NO: 13 oligonucleotide, primer used for amplification and sequencing of STA1, STA1_1055_F SEQ ID NO: 14 oligonucleotide, primer used for amplification and sequencing of STA1, STA1_1768_R SEQ ID NO: 15 oligonucleotide, primer used for amplification and sequencing of STA1, STA1_1671_F SEQ ID NO: 16 oligonucleotide, primer used for amplification and sequencing of STA1, STA1_2384_R SEQ ID NO: 17 oligonucleotide, primer used for amplification and sequencing of STA1, STA1_2267_F SEQ ID NO: 18 oligonucleotide, primer used for amplification and sequencing of STA1, STA1_2951_R SEQ ID NO: 19 oligonucleotide, primer used for amplification and sequencing of STA1, STA1_2901_F SEQ ID NO: 20 oligonucleotide, primer used for amplification and sequencing of STA1, STA1_3550_R SEQ ID NO: 21 oligonucleotide, primer used for amplification and sequencing of STA1, STA1_3474_F SEQ ID NO: 22 oligonucleotide, primer used for amplification and sequencing of STA1, STA1_4169_R SEQ ID NO: 23 oligonucleotide, primer used for amplification and sequencing of STA1, STA1_4051_F SEQ ID NO: 24 oligonucleotide, primer used for amplification and sequencing of STA1, STA1_4746_R SEQ ID NO: 25 oligonucleotide, primer used for amplification and sequencing of STA1, STA1_4657_F SEQ ID NO: 26 oligonucleotide, primer used for amplification and sequencing of STA1, STA1_5201_R SEQ ID NO: 27 CRISPR/Cas9 repair oligonucleotide, re-pair_oligo_promoter_deletion

DETAILED DESCRIPTION OF THE INVENTION

The present invention relates to a method for determining a yeast having extracellular glucoamylase STA1p activity in a sample, or more specifically to a method for genetically differentiating diastatic and non-diastatic yeasts carrying the STA1 gene. In one embodiment said method comprises detecting the presence or absence of an alteration, more specifically a deletion, in the promoter of STA1 gene in a sample.

In one embodiment the presence of the deletion in the promoter of STA1 gene indicates decreased diastatic ability of the yeast compared to a yeast having STA1 gene without a deletion in the promoter region. In one embodiment the presence of the deletion in the promoter of STA1 gene indicates decreased extracellular glucoamylase STA1p activity of the yeast, e.g. when compared to a yeast (such as a corresponding yeast) having STA1 gene without a deletion in the promoter region. Indeed, the inventors of the present disclosure were able to show that said deletion in the promoter of STA1 gene greatly decreases diastatic ability and the expression of STA1.

In one embodiment the absence of the deletion in the promoter of STA1 gene indicates diastatic ability, e.g. high diastatic ability, of the yeast. In one embodiment the absence of the deletion in the promoter of STA1 gene indicates the presence of extracellular glucoamylase STA1p activity of the yeast.

Indeed, the present invention enables determining the presence of a yeast having e.g. high, low or intermediate extracellular glucoamylase STA1p activity. In a specific embodiment yeast strains with the deletion have low or very low levels of STA1p activity but it is not completely absent.

As used herein STA1 gene refers to a gene encoding STA1p, which is a glucoamylase (glucan 1,4-alpha-glucosidase), i.e. an exoamylase which cleaves 1,4-α-glycosidic bonds from the nonreducing end of the glycosidic chains releasing D-glucose, thus increasing the content of fermentable carbohydrates and reducing the nonfermentable dextrins. Glucoamylase is classified as EC 3.2.1.3. In one embodiment all isozymes, isoforms and variants are included with the scope of STA1p. As used herein "glucoamylase STA1p activity" refers to exoamylase activity cleaving 1,4-α-glycosidic bonds from the nonreducing end of the glycosidic chains releasing D-glucose. By the inventors of the present disclosure it was proved that STA1p appears to have a central role in enabling maltotriose use during wort fermentation.

As an example, STA1p protein of the *S. cerevisiae* is identified in the scientific article of Kleinman et al. (1988, *Biochem J,* 249:163-170). STA1p refers to not only *S. cerevisiae* STA1p but also to any other homologue from any yeast. *S. cerevisiae* STA1 gene is described for example in the article of Yamashita et al. (1985, *J Bacteriol,* 161:567-573). Examples of suitable open reading frames (ORF) or gene accession numbers include but are not limited to ORF of *S. cerevisiae* and/or gene accession number Genbank X02649.1.

As used herein "decreased activity" or "low activity" of glucoamylase STA1p refers to the presence of decreased activity, less activity, if any, or low activity of said protein STA1p, or decreased or low total protein activity of a yeast or cell, e.g. when compared to a yeast or cell without a deletion in the promoter region of STA1 gene. "Decreased activity or low activity" also comprises a situation, wherein a protein is totally inactivated and e.g. a yeast or cell has no activity of said protein. "Decreased or low protein activity" may result e.g. from down-regulated polypeptide expression, down-regulated gene expression, decreased level of functional glucoamylases, lack of at least part of the gene, lack of protein, the presence of deletions or attenuating mutations in a gene encoding said glucoamylase STA1p and/or the presence of mutations (e.g. insertions, deletions, substitutions) in STA1p. As used herein "increased activity" or "high activity" of glucoamylase STA1p refers to the presence of higher activity, more activity or high activity of a protein, or higher or high total protein activity of a yeast or cell, e.g. when compared to a yeast or cell with a deletion in the promoter region of STA1 gene. "Increased or high protein activity" may result e.g. from up-regulated or normal polypeptide expression, up-regulated or normal gene expression, increased or normal level of functional glucoamylases, lack of deletions or attenuating mutations in the gene encoding said glucoamylase STA1p, and/or the presence of enhancing mutations in STA1p or STA1 gene.

In a specific embodiment “decreased activity of glucoamylases” or “low activity of glucoamylases” or “decreased level of functional glucoamylases” refers to a situation, wherein a yeast or cell comprising or lacking glucoamylases is not able to grow in beer, e.g. during 3 weeks incubation at 25 °C (FIG. 3A, 3D). In another specific embodiment “increased activity of glucoamylases” or “high or normal activity of glucoamylases” or “increased or normal level of functional glucoamylases” refers to a situation, wherein a yeast or cell comprising glucoamylases has the ability to grow in beer, and consume dextrin from the beer, e.g. during 3 weeks incubation at 25 °C (FIG. 3A, 3D).

In one embodiment of the present invention the yeast comprises a deletion in the promoter area of STA1 gene, thereby reducing expression of said gene. In a very specific embodiment the deleted region comprises an upstream activation sequence, shown to increase expression of the STA1 gene.

As used herein “extracellular activity” refers to an activity, which is present outside of the cell. Said expression is opposite to the expression intracellular.

In a specific embodiment of the invention the presence or absence of the deletion in the promoter area of STA1 gene is detected by measuring the level of STA1p activity in a sample. Optionally a molecular method or a microbiological method can be used in combination with measuring the level of STA1p activity in a sample.

Glucoamylase STA1p activity can be measured by any method known in the field. The presence, absence or level of protein activities e.g. in a cell or yeast can be detected or measured by any suitable method known in the art. Non-limiting examples of suitable detection and/or measuring methods include enzymatic assays, PCR based assays (e.g., multiplex PCR, qPCR, RT-PCR, RT-qPCR), immunological detection methods (e.g., antibodies specific for said proteins), or any method described in the examples of the present disclosure or related to any of FIGS. 1-3 and 6, and any combination thereof. Methods of the examples include but are not limited to PCR based assays (e.g., multiplex PCR, qPCR, RT-PCR, RT-qPCR), HPLC, differential refractometer, organic acid analysis columns, sequencing, visualization e.g. on agarose gels, dextrin fermentation or consumption and analyzing, growth on starch agar and analyzing, growth in beer (spoilage potential) and analyzing, wort fermentation and analyzing, analyzing sugar consumption optionally together with analyzing dextrin consumption, and any combination thereof.

Expression or increased expression can be proved for example by western, northern or southern blotting or quantitative PCR or any other suitable method known to a person skilled in the art.

In one embodiment of the invention the presence of the deletion in the promoter of STA1 gene results in decreased ethanol formation, carbon dioxide formation, hydrolysis of malto-oligomers and/or diastatic capability of the yeast compared to another yeast lacking the deletion in the promoter of STA1 gene.

The method of the present invention, wherein the method comprises detecting the presence or absence of a deletion in the promoter of STA1 gene in a sample, may further comprise detection of one or more genes or any alterations thereof. In one embodiment the method further comprises detecting the presence or absence of STA1 gene. E.g. if two different probes or primer pairs are utilized, it is possible to detect strains, which carry the STA1 gene with the promoter deletion, and those strains, which carry the STA1 gene. E.g. by using STA1_UAS_Fw (SEQ ID NO: 2) and/or STA1_UAS_Rv (SEQ ID NO: 3) primers either alone or together with SD-5A (SEQ ID NO: 5) and/or SD-6B primers (SEQ ID NO: 6) (see table 2), it is possible to determine the presence or absence of a deletion in the promoter area of STA1 gene. Alternatively e.g. STA1_UAS_Q_Fw (SEQ ID NO: 4) and/or STA1_UAS_Rv (SEQ ID NO: 3) primers either alone or together with other primers can be used to determine the presence or absence of a deletion in the promoter area of STA1 gene.

Genetic methods for determining a yeast having extracellular glucoamylase STA1p activity in a sample may also be combined with any other methods known in the field of biotechnology. E.g. in a specific embodiment the method of the present invention may optionally further comprise a microbiological detection method such as detection through culturing yeasts on specialized selective growth media.

In a very specific embodiment the non-spoilage yeast strains which carry the STA1 gene (i.e. those that get flagged as false positives using the currently available genetic test) have a 300-1600 bp deletion (such as 500-1400 bp, 800-1300 bp, or 1000-1200 bp deletion, e.g. 1162 bp deletion) in the promoter region of the STA1 gene. This region contains an upstream activation sequence, which has been shown to increase expression of the STA1 gene. In a specific embodiment the deletion comprises or is a deletion of nucleotides 1127-2288 as numbered in SEQ ID NO: 1, or the deletion is a deletion within nucleotides 1127-2288 as numbered in SEQ ID NO: 1.

Any method or tools known in the field of biotechnology can be utilized for detecting the deletion of the STA1 gene, e.g. a deletion in the promoter area of said gene. In one embodiment the presence or absence of the deletion is detected by a molecular method, optionally by utilizing one or more primers and/or a probe. In one embodiment the molecular method is a polymerase chain reaction (PCR, e.g. multiplex PCR, qPCR, RT-PCR, RT-qPCR) and the method optionally further comprises agarose gel electrophoresis of the product obtained from the PCR. In a very specific method the PCR is a quantitative PCR. In another embodiment the molecular method is a Southern blot, northern blot or whole genome sequencing. In a very specific embodiment the presence or absence of the deletion is detected by a molecular method in combination with a microbiological method or with analysing the level of STA1p activity in a sample.

In one embodiment the method of the present invention comprises allowing a primer or probe capable of hybridizing with the promoter of STA1 gene to contact or hybridize with the polynucleotide, DNA or RNA of the sample or obtained from the sample, e.g. in stringent hybridization conditions. In a specific embodiment of the invention detecting the presence or absence of the deletion in the promoter of STA1 gene is carried out by allowing a primer or probe capable of hybridizing with the promoter of STA1 gene within nucleotides 1127-2288 as numbered in SEQ ID NO: 1 to hybridize with the DNA or RNA obtained from the sample. In a very specific embodiment a further primer and/or probe are used for detecting STA1 and/or another gene.

The present invention further relates to a primer, primer pair or probe that binds specifically to the STA1 gene. Said primer or probe can be used to differentiate spoilage and non-spoilage yeast strains, said non-spoilage strains comprising a deleted promoter region, optionally e.g. highly and poorly diastatic strains. A primer of the present invention is capable of hybridizing with STA1 gene of a yeast, more specifically with the promoter of STA1 gene, e.g. within nucleotides 1127-2288 as numbered in SEQ ID NO: 1. A probe of the present invention is capable of hybridizing with STA1 gene of a yeast, more specifically with the promoter of STA1 gene, e.g. within or at least partially within nucleotides 1127-2288 as numbered in SEQ ID NO: 1. In other words, in one embodiment a primer or probe, which is not able to bind STA1 in the presence of the promoter deletion, is suitable for the present invention. "At least partially" refers to a situation wherein some nucleotides of a probe hybridize with STA1 gene within the nucleotides 1127-2288 as numbered in SEQ ID NO: 1, and some nucleotides hybridize with STA1 gene outside of the region of nucleotides 1127-2288 as numbered in SEQ ID NO: 1, in a situation wherein there is no deletion in the promoter area of STA1.

A primer pair of the present invention comprises two primers capable of hybridizing with STA1 gene of a yeast, wherein at least one of said primers is capable of hybridizing with the promoter of STA1 gene, e.g. within nucleotides 1127-2288 as numbered in SEQ ID NO: 1. In one embodiment both of two primers are capable of hybridizing with the promoter of STA1 gene, e.g. within nucleotides 1127-2288 as numbered in SEQ ID NO: 1. In another embodiment the other primer of the primer pair hybridizes with the STA1 gene outside the promoter region nucleotides 1127-2288 as numbered in SEQ ID NO: 1.

Optionally the primer pair of the present invention can be used together with other primers or probes, e.g. a primer pair for detecting STA1 in a PCR reaction. The aim may thus be to detect the presence of both the STA1 gene and the upstream activation sequence in the promoter which renders the strain a spoilage strain.

In a specific embodiment of the method or for the primer pairs of the invention the PCR reaction for a spoilage strain carrying STA1 may e.g. result in two PCR products of different sizes, which optionally can be separated on an agarose gel using electrophoresis, and/or the PCR reaction for non-spoilage strains carrying STA1 may result in only a single PCR product. In another embodiment the PCR reaction for a spoilage strain carrying STA1 may e.g. result in one PCR product, which optionally can be shown on an agarose gel using electrophoresis, and/or the PCR reaction for non-spoilage strains carrying STA1 may result in no PCR products. As an example, STA1_UAS_Fw (SEQ ID NO: 2) and/or STA1_UAS_Rv (SEQ ID NO: 3) primers (see table 2) can be used to obtain one PCR product in a case, wherein there is no deletion in the promoter of STA1 gene (e.g. visualized as one band in the agarose gel) and no PCR products in a case, wherein there are deletions in the promoter of STA1 gene. In another specific example, STA1_UAS_Fw (SEQ ID NO: 2) and STA1_UAS_Rv (SEQ ID NO: 3) primers can be used together with a further primer or primers such as SD-5A (SEQ ID NO: 5) and/or SD-6B (SEQ ID NO: 6) (see table 2). In such a case, two PCR products can be obtained in a case, wherein there is no deletion in the promoter of STA1 gene (e.g. visualized as two bands in the agarose gel) and one PCR product in a case, wherein there is a deletion in the promoter of STA1 gene.

In the method or tools of the present invention a primer, primer pair or probe capable of hybridizing STA1 gene of the yeast can be of any length, optionally capable of hybridizing in stringent conditions. In one embodiment of the method, primer, primer pair, probe or kit of the invention the primer or probe capable of hybridizing STA1 gene of the yeast is at least 15 nucleotides, e.g. 18-50 nucleotides, 18-40 nucleotides, 18-30 nucleotides, 18-25 nucleotides, 19-24 nucleotides, 20-23 nucleotides, or 20-22 nucleotides. In a specific embodiment of the method, primer, primer pair or kit, one or several primers capable of hybridizing with the promoter of STA1 gene are selected from the group consisting of a nucleotide sequence as shown in SEQ ID NO: 2, a nucleotide sequence as shown in SEQ ID NO: 3, a nucleotide sequence as shown in SEQ ID NO: 4, and any combination thereof.

A person skilled in the art is able to design suitable hybridizing conditions for the primers or probes. In one embodiment hybridization of the present methods, primers or probes is performed under stringent conditions that allow specific binding between a primer or probe and the target nucleotide sequence of STA1 gene. Such stringent conditions for hybridization are sequence-dependent and varied depending on environmental parameters. In a specific embodiment the stringent conditions are high stringent conditions. For example, stringent hybridization conditions can comprise 50-80 °C (such as 55-75 °C or 60-72 °C) at least 10-30 sec (e.g. at least 15 sec), or at least one or more minutes, e.g. one or more times as is the case during a PCR reaction.

A kit of the present invention for genetic testing comprises a primer, primer pair or probe of the invention and optionally reagents for performing said genetic testing. As used herein "genetic testing" refers to testing the presence or absence of a deletion in the promoter of STA1 gene. In a specific embodiment the kit is for the method of the present invention.

Reagents suitable to be used for performing genetic testing include but are not limited to reaction solutions (e.g. solutions for a PCT based reaction) and/or washing solutions, buffers and enzymes. In one embodiment additional tools for detecting the presence or absence of a deletion in the promoter of STA1 gene include but are not limited to detection means selected from the group comprising labels, colouring agents, and antibodies or antigen binding fragments specific for STA1p. Detection mode of the method or kit of the present invention can be any conventional detection mode including but not limited to e.g. colorimetric or fluorescent detection modes.

In general, the presence or absence of a deletion in the promoter of STA1 gene can be detected by any suitable method or tools known in the art suitable for detecting genetic alterations. Optionally the kit or method of the present invention may also comprise use of any suitable statistical methods or tools or instructions related thereto, respectively, known to a person skilled in the art.

In one embodiment the kit further comprises instructions for carrying out said genetic testing. Said instructions may include but are not limited to instructions selected from the group consisting of instructions for carrying out the genetic testing, instructions for carrying out a PCR based method, conditions of the PCR reaction, instructions for separating the PCR products e.g. in electrophoresis, and instructions for interpreting the results (e.g. results of the PCR based reaction optionally wherein the PCR products have been separated by electrophoresis and are visualized on an agarose gel).

In a very specific embodiment of the invention the kit comprises a primer, primer pair or probe of the invention and optionally reagents for performing said genetic testing, and optionally control samples and optionally instructions for carrying out genetic testing. Control samples may be selected e.g. from a sample comprising a deletion in the promoter region of STA1 gene, a sample lacking a deletion in the promoter region of STA1 gene, or combination thereof. In one embodiment the kit of the present invention comprises tools for detecting STA1 gene and/or other genes or alterations thereof.

In one embodiment of the invention the primer, primer pair, probe or kit is for detecting the presence or absence of a deletion in the promoter of STA1 gene in a yeast, optionally in a sample.

A sample which can be analyzed with the method or tools of the present invention includes any sample preferably comprising genetic material or a yeast. In one embodiment the sample is a food sample, biological sample, environmental sample, sample from a facility or surface, air sample or water sample, or selected from the group consisting of a product comprising a substrate for glucoamylase activity, a product of brewing industry, alcoholic beverage, beer, rice wine, sake, and soy sauce. As used herein "a substrate for glucoamylase activity" refers to any substrate comprising glycosidic chains having 1,4-α-glycosidic bonds in the nonreducing end. Said substrate can be selected e.g. from the group consisting of starch, maltodextrin and oligosaccharides.

In one embodiment the sample has been obtained from food (including drinks and beverages), which is to be packed in a bottle, can, keg, box or package. Indeed, the presence of e.g. normal, high or significant extracellular glucoamylase STA1p activity in said sample causes high or increased carbon dioxide and ethanol levels thereby increasing the risk of exploding bottles, cans, keg, box or packages.

The methods and tools of the present invention are for yeasts. Therefore, STA1 genes utilized in the present invention are yeast genes. In one embodiment of the invention the yeast belongs to a genus *Saccharomyces*, e.g. the yeast is selected from the group consisting of species known as, or formerly known as, *S. arboricolus, S. bayanus, S. boulardii, S. bulderi, S. cariocanus, S. cariocus, S. cerevisiae, S. chevalieri, S. dairenensis, S. ellipsoideus, S. eubayanus, S. exiguus; S. florentinus, S. fragilis, S. kluyveri, S. kudriavzevii, S. jurei, S. martiniae, S. mikatae, S. monacensis, S. norbensis, S. paradoxus, S. pastorianus, S. spencerorum, S. turicensis, S. unisporus, S. uvarum*, and *S. zonatus*. In a specific embodiment said yeast is *S. cerevisiae.*

Also, the present invention relates to use of the primer, primer pair, probe or kit of the present invention for detecting the presence or absence of a deletion in the promoter of STA1 gene in a yeast.

And still furthermore, the present invention concerns a genetically modified yeast that has been genetically modified to decrease extracellular glucoamylase STA1p activity. Also, the present invention concerns a yeast that has been modified by adaptive evolution strategy to decrease extracellular glucoamylase STA1p activity.

The present invention relates to a (genetically) modified yeast comprising a deletion in the promoter of STA1 gene, e.g. said deletion comprising or being within nucleotides 1127-2288 as numbered in SEQ ID NO: 1. Methods for making any genetic modifications or modifying microorganisms by adaptive evolution strategy are generally well known by a person skilled in the art and are described in various practical manuals describing laboratory molecular techniques. The knowledge gained during the study of the present disclosure can be used for obtaining modified yeasts comprising specific alterations. The construction of a yeast in which one or more genes or parts thereof are genetically modified is within the skills of an artisan. Some examples of the general procedure and specific embodiments are described in the Examples chapter. In one embodiment of the invention the genetic modification has been carried out by a CRISPR/Cas9 based method.

In a specific embodiment the yeast that has been genetically modified to decrease extracellular glucoamylase STA1p activity in a yeast belongs to a genus *Saccharomyces* or in a more specific embodiment said yeast is *S. cerevisiae.*

The yeast of the present invention may also contain other genetic modifications than the modifications of STA1 gene, e.g. deletions in the promoter region of the STA1 gene as specifically described in this disclosure.

As used in the present disclosure, the terms "polypeptide" and "protein" are used interchangeably to refer to polymers of amino acids of any length.

As used herein "polynucleotide" refers to any polynucleotide, such as single or double-stranded DNA (genomic DNA or cDNA) or RNA, comprising a nucleic acid sequence encoding a polypeptide in question or a conservative sequence variant thereof. Conservative nucleotide sequence variants (i.e. nucleotide sequence modifications, which do not significantly alter biological properties of the encoded polypeptide) include variants arising from the degeneration of the genetic code and from silent mutations.

It will be obvious to a person skilled in the art that, as the technology advances, the inventive concept can be implemented in various ways. The invention and its embodiments are not limited to the examples described below but may vary within the scope of the claims.

EXAMPLES

Materials & Methods

Yeast Strains

A list of strains used in this study can be found in Table 1.

TABLE 1

Yeast strains used in the study.

| Code | Alternative name | Species | STA1 | 1162 bp deletion in STA1 promoter | Source |
|---|---|---|---|---|---|
| A15 | VTT-A83015 | *S. pastorianus* | − | NA | VTT Culture Collection |
| A60 | VTT-A75060 | *S. cerevisiae* | − | NA | VTT Culture Collection |
| WLP007 | | *S. cerevisiae* | − | NA | White Labs Inc. |
| WLP023 | | *S. cerevisiae* | − | NA | White Labs Inc. |
| TUM PI BA 109 | | *S. cerevisiae* | + | − | BLQ Weihen-stephan |
| TUM 3-D-2 | | *S. cerevisiae* | + | − | BLQ Weihen-stephan |
| TUM PI BA 45 | | *S. cerevisiae* | + | + | BLQ Weihen-stephan |
| TUM PI BB 105 | | *S. cerevisiae* | + | + | BLQ Weihen-stephan |
| TUM PI BA 31 | | *S. cerevisiae* | + | + | BLQ Weihen-stephan |

TABLE 1-continued

Yeast strains used in the study.

| Code | Alternative name | Species | STA1 | 1162 bp deletion in STA1 promoter | Source |
|---|---|---|---|---|---|
| TUM 71 | | *S. cerevisiae* | + | − | BLQ Weihen-stephan |
| TUM 3-H-2 | | *S. cerevisiae* | + | − | BLQ Weihen-stephan |
| WY3711 | | *S. cerevisiae* | + | − | Wyeast Laboratories |
| WLP565 | | *S. cerevisiae* | + | + | White Labs Inc. |
| WLP566 | | *S. cerevisiae* | + | + | White Labs Inc. |
| WLP570 | | *S. cerevisiae* | + | + | White Labs Inc. |
| WLP644 | | *S. cerevisiae* | + | + | White Labs Inc. |
| Ontario Farmhouse | | *S. cerevisiae* | + | + | Escarpment Laboratories |
| Wild Thing | | *S. cerevisiae* | + | + | Escarpment Laboratories |
| A62 | VTT-A81062 | *S. cerevisiae* | + | + | VTT Culture Collection |

Dextrin Fermentation

The ability to ferment dextrin was tested in minimal growth media with dextrin as the sole carbon source. Strains were grown overnight in YP-Glucose (2%), after which 20 μL of overnight culture was used to inoculate 2 mL microcentrifuge tubes containing 1 mL of dextrin media (0.67% YNB without amino acids, 1% dextrin from potato starch). The tubes were incubated at room temperature for 3 weeks. Samples were drawn each week and analysed with HPLC to determine the amount of dextrin consumed.

Growth on Starch Agar

The ability to grow on solid media containing starch as the sole carbon source was tested on agar plates (Meier-Dörnberg et al., 2018). Agar plates were prepared containing 0.67% YNB/wo amino acids, 1.5% soluble starch and 40 mg/L bromophenol blue. pH was adjusted to 5.2 with 0.1 M HCl. Yeast strains were grown overnight in YP-Glucose, washed twice with sterile MQ-$H_2O$, and then resuspended to an OD600 of 1. Aliquots of yeast suspension (100 μL) were spread out on agar plates. The plates were incubated in an anaerobic jar (Anoxomat AN2CTS, Mart Microbiology) at 25 °C for four weeks.

Growth in Beer

The spoilage potential of STA1+ strains was assessed by growing them in beer. Beer was produced by inoculating one litre of 10° Plato all-malt wort with *S. pastorianus* A15 and fermenting at 25 °C for one week. The beer was centrifuged and sterile-filtered (0.45 μm, followed by 0.22 μm). The beer was analysed with HPLC and determined to contain less than 1 g/L each of maltose and maltotriose. Yeast strains were grown overnight in YP-Glucose, washed twice with sterile MQ-$H_2O$, and then resuspended to an OD600 of 1. Sterile-filtered beer (4750 μL) was inoculated with 250 μL of pre-culture for a starting OD600 of 0.05. The beer cultivations were incubated statically in an anaerobic jar (Anoxomat AN2CTS, Mart Microbiology) at 25 °C for three weeks. The optical density was monitored once a week, and the final amount of dextrin consumed was analysed with HPLC after three weeks.

Wort Fermentation and Analysis

Concentrations of fermentable sugars and dextrin were measured by HPLC using a Waters 2695 Separation Module and Waters System Interphase Module liquid chromatograph coupled with a Waters 2414 differential refractometer (Waters Co., Milford, MA, USA). An Aminex HPX-87H organic acid analysis column (300× 7.8 mm, Bio-Rad) was equilibrated with 5 mM $H_2SO_4$ (Titrisol, Merck, Germany) in water at 55 °C and samples were eluted with 5 mM $H_2SO_4$ in water at a 0.3 ml/min flow rate.

Sequencing of STA1

The STA1 open reading frame and promoter (2.5 kb upstream) were amplified by PCR and then sequenced using Sanger sequencing. A nested PCR approach was used to prevent PCR primers from amplifying fragments from FLO11 and SGA1. First, a 5.2 kb amplicon was produced using primers STA1_Full_Fw and STA1_Full_Rv (Table 2). The amplicon was diluted 1:500 in MQ-$H_2O$ and used as template DNA for the ten PCR reactions described in Table 2. All PCR reactions were carried out with Phusion High-Fidelity PCR Master Mix with HF Buffer (Thermo Scientific) and primer concentrations of 0.5 μM. Amplicons were cleaned using the QIAquick PCR purification kit of Qiagen (Hilden, Germany), and sequenced at Seqlab-Microsynth (Goettingen, Germany). Sequences were aligned in Geneious 10.0.9 (Biomatters).

TABLE 2

Oligonucleotides used in the study.

| Name | Sequence (5' > 3') | Reference |
|---|---|---|
| Primers used for amplification and sequencing of STA1 ORF and upstream region | | |
| STA1_Full_Fw | TGGAATGAACAGCGCCAAGT | This study (SEQ ID NO: 7) |
| STA1_Full_Rv | AGTGGGAGAAAAAGGTGGCC | This study (SEQ ID NO: 8) |
| STA1_24_F | AATGAACAGCGCCAAGTAGC | This study (SEQ ID NO: 9) |

TABLE 2-continued

Oligonucleotides used in the study.

| Name | Sequence (5' > 3') | Reference |
|---|---|---|
| STA1_546_R | TTGAAAGCTATGTGCAGTTGG | This study (SEQ ID NO: 10) |
| STA1_482_F | TGTCCCCTAATGTATCCCTCA | This study (SEQ ID NO: 11) |
| STA1_1148_R | AAATCTTACCCGTGGATCCTTT | This study (SEQ ID NO: 12) |
| STA1_1055_F | CCCAAAATTCATTCGTAGCC | This study (SEQ ID NO: 13) |
| STA1_1768_R | TATGCGATGTCCCAGTACGA | This study (SEQ ID NO: 14) |
| STA1_1671_F | TGTCAGGCATTGCACAAACT | This study (SEQ ID NO: 15) |
| STA1_2384_R | CAATTGAGAACCCTTCAACAA | This study (SEQ ID NO: 16) |
| STA1_2267_F | AGGGCAGTTTTATTTACCTTAACA | This study (SEQ ID NO: 17) |
| STA1_2951_R | AAGTGGTTGTTGATTCCGATG | This study (SEQ ID NO: 18) |
| STA1_2901_F | TCCATGTTCAACCAGTCCAA | This study (SEQ ID NO: 19) |
| STA1_3550_R | CTGTCGCTGGAGCCACTC | This study (SEQ ID NO: 20) |
| STA1_3474_F | CTTGATGAATGGGACAGTGG | This study (SEQ ID NO: 21) |
| STA1_4169_R | GACCGTTCTGAGGCGTTAAA | This study (SEQ ID NO: 22) |
| STA1_4051_F | TGGAATTCTTCCGGATTTGA | This study (SEQ ID NO: 23) |
| STA1_4746_R | GGTTTGATTGAAGGCAGGTG | This study (SEQ ID NO: 24) |
| STA1_4657_F | AGCGAGCTGGTATTCTCCAA | This study (SEQ ID NO: 25) |
| STA1_5201_R | ACACGCTTTGGACATCATCA | This study (SEQ ID NO: 26) |
| Primers used for the detection of STA1 | | |
| SD-5A | CAACTACGACTTCTGTCATA | Yamauchi et al., 1998, (SEQ ID NO: 5) |
| SD-6B | GATGGTGACGCAATCACGA | Yamauchi et al., 1998, (SEQ ID NO: 6) |
| Primers used for the detection of intact STA1 promoter | | |
| STA1_UAS_Fw | CCTGGCTCAAATTAAACTTTCG | This study, (SEQ ID NO: 2) |
| STA1_UAS_Rv | ACCACCAATAGGCAATAGAAA | This study, (SEQ ID NO: 3) |
| STA1_UAS_Q_Fw | CAAGGCAATCAGTTAAAAGA | This study, (SEQ ID NO: 4) |

TABLE 2-continued

| Oligonucleotides used in the study. | | |
|---|---|---|
| Name | Sequence (5' > 3') | Reference |
| Primers used in quantitative PCR | | |
| Sdia-f | TTCCAACTGCACTAGTTCCTAGAGG | Brandl, 2006 (SEQ ID NO: 28) |
| Sdia-r | GAGCTGAATGGAGTTGAAGATGG | Brandl, 2006 (SEQ ID NO: 29) |
| UBC6_F | GATACTTGGAATCCTGGCTGGTCTGTCTC | Teste et al., 2009 (SEQ ID NO: 30) |
| UBC6_R | AAAGGGTCTTCTGTTTCATCACCTGTATTT GC | Teste et al., 2009 (SEQ ID NO: 31) |
| ALG9_F | CACGGATAGTGGCTTTGGTGAACAATTAC | Teste et al., 2009 (SEQ ID NO: 32) |
| ALG9_R | TATGATTATCTGGCAGCAGGAAAGAACTT GGG | Teste et al., 2009 (SEQ ID NO: 34) |
| CRISPR/Cas9 repair oligos | | |
| re-pair_oligo_promoter_deletion | GACGGGGTATTATGAATAAAGGATCCACG GGTAAGATTTGCTGCGCTCTCTTCTAGTTC AAGAACGGATAACTCATAGAC | This study (SEQ ID NO: 27) |

Multiplex PCR to Detect Presence of Deletion in STA1 Promoter

The presence of the STA1 gene was tested with PCR using the previously published primers SD-5A and SD-6B (Yamauchi et al. 1998). These primers amplify an 868 bp fragment from the STA1 gene. In addition, a new primer pair (STA1_UAS_Fw and STA1_UAS_Rv; Table 2) was designed to detect whether the STA1+ yeast strains had the full promoter sequence. Both primers bind within the 1162 bp region that was found to be deleted in the poorly diastatic strains, and they amplify a 599 bp fragment. Primers were tested in separate and multiplex PCR reactions. PCR reactions were carried out with Phusion High-Fidelity PCR Master Mix with HF Buffer (Thermo Scientific) and primer concentrations of 0.5 μM. The following PCR program was used: 98 °C. 30 sec, (98 °C. 10 sec, 63 °C. 15 sec, 72 °C 30 sec)×30 cycles, 72 °C 10 min. PCR products were separated and visualized on 1.0% agarose gels.

Quantitative PCR to Detect Presence of Deletion in STA1 Promoter

The presence of the STA1 gene was tested with quantitative PCR using the previously published primers Sdia-f and Sdia-r (Brandl, 2006). These primers amplify an 79 bp fragment from the STA1 open reading frame. In addition, a new primer pair (STA1_UAS_Q_Fw and STA1_UAS_Rv; Table 2) was designed to detect whether the STA1+ yeast strains had the full promoter sequence. Both primers bind within the 1162 bp region that was found to be deleted in the poorly diastatic strains, and amplify a 223 bp fragment. The qPCR reactions were prepared with PerfeCTa SYBR® Green SuperMix (QuantaBio, USA) and 0.3 UM of the primers (Table 2). The qPCR reactions were performed on a LightCycler® 480 II instrument (Roche Diagnostics, Switzerland) in two technical replicates on 50 ng template DNA extracted with a YeaStar Genomic DNA kit (Zymo Research, USA). The following program was used: pre-incubation (95 °C for 3 min), amplification cycle repeated 45 times (95 °C for 15 s, 60 °C for 30 s, 72 °C for 20 s with a single fluorescence measurement), melting curve program (65-97 °C with continuous fluorescence measurement), and finally a cooling step to 40 °C.

CRISPR/Cas9 Mediated Deletions

In order to confirm the effect of the 1162 bp deletion that was observed in the STA1 promoter of the poorly diastatic strains, reverse engineering in the highly diastatic *S. cerevisiae* WY3711 strain was performed using the CRISPR/Cas9 system. Plasmid construction was carried out using the plasmid pCC-036 as backbone (Rantasalo et al., 2018, ACS Synth. Biol. 7, 6, 1573-1587). pCC-036 contains yeast codon-optimized Cas9 expressed under TDH3p, guiding RNA (gRNA) expressed under SNR52p, and hygR for selection on hygromycin. The gRNA protospacer sequence, TGGCTCAAATTAAACTTTCG (SEQ ID NO: 34), was designed using CCTop (Stemmer et al., 2015, PLOS One, 12 (4), e0176619). The protospacer sequence was designed to induce a double-stranded break within the region to be deleted and was chosen for minimal off-target activity. A synthetic DNA fragment with the gRNA sequence was ordered from Integrated DNA Technologies, and introduced into the plasmid with restriction enzyme-based techniques (Thermo Scientific, Finland). The ligated plasmid was transformed into *E. coli* TOP10 by electroporation, and plasmid correctness was confirmed by Sanger sequencing. A 80 bp repair oligo (repair_oligo_promoter_deletion SEQ ID NO:27), consisting of adjacent 40 bp sequences homologous to those up- and downstream of the deleted region (Table 2), was also ordered from Integrated DNA Technologies.

Transformation of *S. cerevisiae* WY3711 was performed using a standard lithium acetate-based protocol with 40 minute incubation at 42 °C (Gietz and Woods, 2002, Methods Enzymol. Vol 350, Pages 87-96). Cells were transformed together with 3.6 μg of purified plasmid and 2.5 nmol of repair oligo. The transformed cells were selected on plates containing 300 mg/L Hygromycin B (Sigma-Aldrich). Colony PCR using primer pairs 1055F/2951R and STA1_UAS_Fw/STA1_UAS_Rv was used to confirm successful deletion in the transformed cells. Colonies from selection plates were replated three times onto YPD agar plates to encourage plasmid loss, after which they were stored at −80 °C.

STA1 Transcript Analysis by RT-qPCR

Strains were grown overnight in YP-Glucose, after which four replicate cultures per strain were started by inoculating 20 mL YPGE (1% yeast extract, 2% peptone, 3% glycerol and 2% ethanol) to a starting OD600 of 0.1. Cultures were overnight at 25 °C. (OD600 varied between 2 and 4), after which RNA was isolated from pelleted yeast using hot formamide extraction (Shedlovskiy et al., 2017, *RNA Biol.* Vol 14, issue 12, pages 1722-1726). RNA was precipitated by first diluting 50 μL RNA solution with 25 μL 3 M sodium acetate and 200 μL nuclease-free water, after which 825 μL ice-cold ethanol was added and solutions were stored overnight at −20 °C. The solutions were centrifuged at 16000×g for 30 minutes, after which the pellet was washed with ice-cold 75% ethanol and tubes were centrifuged again at 8000×g for 5 minutes. The supernatant was removed and the pellet was allowed to air-dry for up to 30 minutes, after which the RNA pellet was dissolved in nuclease-free water. The RNA solution was treated with TURBO DNAse (DNA-Free kit, Invitrogen) and the DNAse was subsequently inactivated using the supplied inactivation reagent. RNA was quantified with a Qubit 2.0 fluorometer and its quality was assessed on 1.2% agarose gels (made in 1×TAE buffer).

250 ng of total RNA was reverse-transcribed using a qScript Flex cDNA kit (QuantaBio, USA), using a mixture of supplied oligo-dT and random primers according to kit instructions. The resulting cDNA was diluted 5-fold and 4 μL of diluted cDNA (corresponding to 10 ng of total RNA) was used as template in 20 μL qPCR reactions. The qPCR reactions were prepared with PerfeCTa SYBR® Green SuperMix (QuantaBio, USA) and 0.3 μM of gene-specific primers (Table 2). In addition to using primers specific to STA1, reactions with primers for two housekeeping genes (ALG9 and UBC6) were also performed (Teste et al., 2009, BMC Mol. Biol. 10:99). The qPCR reactions were performed on a LightCycler® 480 II instrument (Roche Diagnostics, Switzerland) in two technical replicates on the reverse-transcribed RNA isolated from four biological replicates. The following program was used: pre-incubation (95 °C for 3 min), amplification cycle repeated 45 times (95 °C for 15 s, 60 °C for 30 s, 72 °C for 20 s with a single fluorescence measurement), melting curve program (65-97 °C with continuous fluorescence measurement), and finally a cooling step to 40 °C. The relative expression of STA1 in the three examined yeast strains was calculated using the 'delta-delta Cr'-method by normalizing expression to that of the two house-keeping genes ALG9 and UBC6 (Pfaffl, 2001, Nucleic Acids Res., Vol 29, Issue 9, Page e45).

Results

Screening of Diastatic Ability

The diastatic ability of eighteen *S. cerevisiae* and one *S. pastorianus* strain (Table 1) was tested using three different tests: growth in beer, growth on starch agar, and fermentation of dextrin as a sole carbon source. Of the eighteen *S. cerevisiae* strains, 15 tested positive for STA1 using the SD-5A/SD-6B primer pair (Yamauchi et al. 1998). Despite carrying the STA1 gene, only five out of 15 strains, were able to grow in beer and on starch agar (FIG. 1). These five strains also fermented dextrin efficiently. All four of the strains that tested negative for STA1 were unable to grow in beer or on starch agar, and did not consume any dextrin.

We then amplified and sequenced the STA1 open reading frame and a 2.5 kb upstream region, to search for polymorphisms that might explain the variation in diastatic ability in the 15 strains that tested positive for STA1. We observed a 1162 bp deletion upstream of STA1 (−1370 to −209 from the start codon) in 10 out of the 15 strains (FIGS. 1-2). This 1162 bp region contains an upstream activation sequence and transcription factor binding site (Kim et al. 2004, Mol. Cell. Biol. 24, 9542-9556; Kim et al., 2004, Mol. Cell. Biol. 24, 7695-7706). Interestingly, the presence of this deletion appeared to coincide with decreased diastatic ability (FIG. 1). The strains with the deletion in the promoter exhibited significantly less diastatic ability in all tests (FIG. 1A-D). We hypothesised that this deletion impedes transcription of STA1, which in turn decreases the amount of STA1-derived glucoamylase produced by the strains.

Confirmation by Reverse Engineering

To confirm that the 1162 bp deletion that was observed in the STA1 promoter had a negative effect on diastatic ability and STA1 expression, we performed reverse engineering aided by the CRISPR/Cas9 system. The gRNA protospacer sequence was designed to cause a double-stranded break within the region to be deleted (FIG. 2E). The 1162 bp region (−1370 to −209 upstream of the STA1 open reading frame) was deleted from the highly diastatic WY3711 strain by transformation with a Cas9- and gRNA-expressing plasmid and an 80 bp double-stranded repair oligo. PCR using primer pairs binding within (STA1_UAS_Fw/STA1_UAS_Rv) and outside the deleted region (1055F/2951R) was used to confirm successful deletion (FIG. 2D).

The deletion strain, WY3711_D1, was then tested for diastatic ability. WY3711, the wild-type strain from which WY3711_D1 was derived, and WLP570, a strain that naturally contains the 1162 bp deletion in the promoter, were included as controls. In all tests the diastatic ability of WY3711_D1 was less than WY3711. When inoculated into beer, WY3711_D1 and WLP570 grew significantly less than WY3711 (FIG. 3A). In contrast to WY3711, WY3711_D1 and WLP570 had also not consumed any dextrin from the beer after 3 weeks (FIG. 3D). When the strains were grown in minimal media with dextrin as the sole carbon source, we saw negligible dextrin consumption after 3 weeks with WY3711_D1 and WLP570 when cultures were incubated anaerobically (FIG. 3B). Interestingly, we observed delayed activity in these strains when cultures were incubated aerobically (FIG. 3C). WY3711 performed similarly in both anaerobic and aerobic conditions, and in both cases consumed significantly more dextrin than the strains with the deletion in the promoter.

To test the effect that the 1162 bp deletion in the STA1 promoter has on the expression of STA1, we performed RT-qPCR analysis on RNA extracted from exponential phase cultures in YPGE. This growth medium was chosen as glucose represses STA1 expression (Kim et al. 2004, *Mol. Cell. Biol.* 24, 7695-7706; Pretorius et al., 1986, *Mol. Cell. Biol.* 6(9):3034-41). We observed a 150-200 fold higher abundance of STA1 mRNA in the samples from WY3711 compared to WY3711_D1 and WLP570, respectively (FIG. 3E). These results suggest that the decreased diastatic ability observed in the STA1+ strains with the 1162 bp deletion is a result of decreased expression of STA1.

Designing Primers for the Detection of the Full STA1 Promoter

To improve the reliability of the molecular detection methods for diastatic *S. cerevisiae*, we designed two new primer pairs that bind within the 1162 bp region that is absent in the poorly diastatic STA1+ strains. These new primers can therefore be used to differentiate whether a strain that has tested positive for STA1 with the SD-5A/SD- 6B primers (Yamauchi et al. 1998) is likely to be highly diastatic or not. The first primer pair (STA1_UAS_Fw/STA1_UAS_Rv) was designed to produce a 599 bp amplicon, and can be used together with the SD-5A/SD-6B primers in a single multiplex PCR reaction (FIG. 2B-C). Here, strains with the full STA1 promoter produce two amplicons (599 and 868 bp), while poorly diastatic strains only produce a single amplicon (868 bp).

In addition, a second primer pair (STA1_UAS_Q_Fw/STA1_UAS_Rv) was also designed to be useable in quantitative PCR reactions where a shorter amplicon is desired. This primer pair produces a 223 bp amplicon. We performed quantitative PCR reactions on DNA extracted from *S. cerevisiae* WY3711, *S. cerevisiae* WLP570 and *S. pastorianus* A15 using both the previously published Sdia-f/Sdia-r primer pair that bind within the STA1 ORF (Brandl, 2006), and our newly designed primer pair that bind within the STA1 promoter. As expected, amplification using the Sdia-f/Sdia-r primer pair was observed for both WY3711 and WLP570 (threshold cycles of 17.0 and 18.9), while no signal above the background was observed for the negative control A15 after 40 cycles. With the new primer pair on the other hand, amplification was only observed for the highly diastatic WY3711 (threshold cycle of 18.4), while no signal above the background was observed for the poorly diastatic WLP570 and the negative control A15 after 40 cycles.

The invention claimed is:

1. A method for determining spoilage potential of a yeast carrying STA1 gene in a sample, wherein the method comprises:

a) allowing a primer or a probe capable of hybridizing with at least a portion of the promoter of STA1 gene to hybridize with a polynucleotide of the sample, wherein said promoter comprises nucleotides 1127-2288 as numbered in SEQ ID NO: 1;

b) detecting a presence or an absence of a natural deletion in the promoter of STA1 gene of the sample, wherein the natural deletion is a deletion of nucleotides 1127-2288 as numbered in SEQ ID NO: 1, and wherein the detecting comprises:

i) performing, with the primer or the probe of step a), a molecular method that generates one or more reaction products from a region of the promoter of STA1 gene that, in a promoter lacking the natural deletion, spans nucleotides 1127-2288 as numbered in SEQ ID NO: 1; and ii) detecting said one or more reaction products and determining, from presence, absence, and/or size of the reaction products, whether the natural deletion is present or absent in the promoter of STA1 gene in the sample;

c) determining that the sample does not include a spoilage yeast strain if the presence of the natural deletion in the promoter of the STA1 gene is detected, or that the sample does include a spoilage yeast strain if the absence of the natural deletion in the promoter of the STA1 gene is detected;

d) if it is determined that the sample does include a spoilage yeast strain: i) recalling or discarding the sample or a product from which the sample is taken; and/or ii) not utilizing one or more yeast strains from the sample for fermentation; and e) if it is determined that the sample does not include a spoilage yeast strain: i) not recalling or discarding the sample or a product from which the sample is taken; and/or ii) utilizing one or more yeast strains from the sample for fermentation.

2. The method of claim 1, wherein the molecular method is a polymerase chain reaction (PCR), optionally a quantitative PCR, and wherein the method optionally further comprises agarose gel electrophoresis of a product obtained from the PCR.

3. The method of claim 1, wherein a further primer and/or probe is used for detecting STA1 and/or another gene.

4. The method of claim 1, wherein the absence of the natural deletion in the promoter of STA1 gene indicates presence of extracellular glucoamylase STA1p activity of the yeast.

5. The method of claim 1, wherein the presence of the natural deletion in the promoter of STA1 gene indicates decreased extracellular glucoamylase STA1p activity of the yeast, or wherein the presence of the natural deletion in the promoter of STA1 gene results in decreased ethanol formation, carbon dioxide formation, hydrolysis of maltotriose and/or diastatic capability of the yeast compared to another yeast lacking the natural deletion in the promoter of STA1 gene.

6. The method of claim 1, wherein the method further comprises detecting the presence or absence of STA1 gene.

7. The method of claim 1, wherein the sample is a food sample, biological sample, environmental sample, sample from a facility or surface, air sample or water sample, or selected from the group consisting of a product comprising a substrate for glucoamylase activity, a product of brewing industry, alcoholic beverage, beer, rice wine, sake, and soy sauce.

8. The method of claim 1, wherein step a) uses a primer capable of hybridizing with at least a portion of the promoter of STA1 gene, wherein said promoter comprises nucleotides 1127-2288 as numbered in SEQ ID NO: 1, and wherein said primer is selected from the group consisting of a sequence as shown in SEQ ID NO: 2, a sequence as shown in SEQ ID NO: 3 and a sequence as shown in SEQ ID NO: 4.

9. The method of claim 1, wherein step a) uses a primer pair comprising two primers capable of hybridizing with STA1 gene of a yeast and at least one of said primers is capable of hybridizing with at least a portion of the promoter of STA1 gene, wherein said promoter comprises nucleotides 1127-2288 as numbered in SEQ ID NO: 1, and wherein said primer is selected from the group consisting of a sequence as shown in SEQ ID NO: 2, a sequence as shown in SEQ ID NO: 3 and a sequence as shown in SEQ ID NO: 4.

10. The method of claim 9, wherein both of the two primers are capable of hybridizing with at least a portion of the promoter of STA1 gene, wherein said promoter comprises nucleotides 1127-2288 as numbered in SEQ ID NO: 1.

11. The method of claim 1, wherein the yeast belongs to a genus *Saccharomyces* or is *Saccharomyces cerevisiae.*

* * * * *

SEQUENCE LISTING

```
<160> NUMBER OF SEQ ID NOS: 34

<210> SEQ ID NO 1
<211> LENGTH: 5225
<212> TYPE: DNA
<213> ORGANISM: Saccharomyces cerevisiae

<400> SEQUENCE: 1

ggaatgaaca gcgccaagta gcactggaca aactgcagaa agtattagta cttgctttat     60

tccgtgtatc gtactttagg tcgtcagttt tacacttcgg tacgcaaatg aaaataaaaa    120

gctcattcac aacttagaca caatttcgcc atttacaagt agctgaagag tccatctatc    180

gaattatgaa tgatgctatt ttaaatatcg tcgttgctgc actcgttttc catgttcttt    240

ttatccacac atccgatgtt ttatttacag ttgagcatct cagggccagc gacaaatata    300

aacatattat actcaaaatg aagctcgttg aaaagaggat atttcttaac ctcttttaca    360

gtgttttcaa caccttttca tctgtgtgcc atgtcagatt aaggatgctc aacttttcga    420

attattatta caaatttcaa agaaattact attccttttt gtcccctaat gtatccctca    480

tttcataccg tcgttttggg gttccaactg cacatagctt tcaagtgtgg ttttacggta    540

agaacaaccc ccccatcggt tggtgcggaa tactttccta ttctcatcga gagccgagcc    600

atacacctaa ggtggacaga aagctaaaat tccaaaacag aaaaatctaa catctttgct    660

cccttacaag taggaacgct agcgtatcaa cccatctcca gatttgccca gcatttctgt    720

agaacaccca atgcgaatga agactaatga atattttaaa ggcaaaaaat aggaaaagtt    780

taattattga tggttctcac caccgcaaaa cggtcacttg catgcattga ggacatgcat    840

ctgcagtact tgtttttctc gaatgttttt taccatctct tttttcctta tctgagctgc    900

tgacgcagac ggacattgtt tcatatttcg aaagctgtgc gggaaaacgg acccaaacac    960

gaatgtggat gcgctaatcg gtatttccat ctcatgaaac ctgctacttt ttcagtgctc   1020

ttcgtatgca tttcccaaaa ttcattcgta gccttgtcaa cttagactca gttccacggc   1080

gtgcaggacg gggtattatg aataaaggat ccacgggtaa gatttgttct atgttttagg   1140

tatggagttt tgtaccacaa aactttagga ataccggatt gtgtgcctac gccagcccca   1200

gagtatgttc tcacggctgt aattcctagt gatcttttcc tggctcaaat taaactttcg   1260

cggcaggaaa aaaaaggctt tttctttttt gtgtttcagt ttctcggaat gtggcattac   1320

ataagcataa tccttttggg gtgtgcctgg aaagttcaaa ttaagggttt tttcttttgt   1380

tttcttgaca agaaaatgtt gcccaaagag tttcggccgt tattttccta tccaagtggg   1440

tcctttttgt ctttagtcct tctctggggc tagcgatcgc tgcaaaatta ggcttcactg   1500

gtacgagtta actttttttc ttttttttg tcatcctttt ctttggggct aaaaatggac   1560
```

-continued

```
ttccctttc tttttctttg ttgcagcagt ggcttcaaag aactgctgat tgctcaaggc   1620
aatcagttaa aagaaaaatt agcttttttt gtcaggcatt gcacaaactt ttttatttct   1680
gcctatactc ttagacagat cagtcattca tgttgtcttt ttaacggtcg tactgggaca   1740
tcgcatacct tgagattccg taattaggtg caacaatacg ggcacaactc attctgcggt   1800
atcttcacgg acagaatttc tattgcctat tggtggtgtg attaacaatt ggaagcgcag   1860
agcttagaat ggattttcaa ttcaatggat ttggaggtat tcgtttgttt actaatattt   1920
actttgagga cattgcccaa ccctaaaagt gcctgttcca gaacagaata acattatgat   1980
acgttttcct gaccgctgag caatttaaag caattagtag ggtacgattg tttctagaga   2040
aatgtgggtc atctttttag gtccgttctc ttctgatgag gtaaccttta caaaaatgtc   2100
atggagttac caattgggat tcaaggcatc atcacaaatat acttcgttct tttacggaga  2160
aattaagctc tttctacttt gaattaactg ttagacttgt cttatctgag aaatgtccgt   2220
gttcaaatta aataaaaatt tagggcagtt ttatttacct taacaaatat gttcaagcat   2280
ttacgttact gcgctctctt ctagttcaag aacggataac tcatagactt acctgtacaa   2340
gttgttgaag ggttctcaat tgataaaaaa ggatcttttg cttcctaaac taaacctata   2400
aaaagcaccc tattcatcag ttataatctc ttgtcatgtt gtggttctaa ttgaaaatat   2460
actttggtag gcctcaaaaa tccatatacg cacactatgc aaagaccatt tctacttgct   2520
tatttggtcc tttcgcttct atttaactca gctttgggtt ttccaactgc actagttcct   2580
agaggatcct cctctagcaa catcacttcc tccggtccat cttcaactcc attcagctct   2640
gctactgaaa gcttttctac tggcactact gtcactccat catcatccaa ataccctggc   2700
agtaaaacag aaacttctgt ttcttctaca accgaaacta ccattgttcc aactacaact   2760
acgacttctg tcataacacc atcaacaacc actattacca ctacggtttg ctctacagga   2820
acaaactctg ccggtgaaac tacttctgga tgctctccaa agaccattac aactactgtt   2880
ccatgttcaa ccagtccaag cgaaaccgca tcggaatcaa caaccacttc acctaccaca   2940
cctgtaacta cagttgtctc aaccaccgtc gttactactg agtattctac tagtacaaaa   3000
caaggtggtg aaattacaac tacatttgtc accaaaaaca ttccaaccac ttacctaact   3060
acaattgctc caacttcatc agtcactacg gttaccaatt tcaccccaac cactattact   3120
actacggttt gctctacagg aacaaactct gccggtgaaa ctacctctgg atgctctcca   3180
aagactgtca caacaactgt tccttgttca actggtactg gcgaatacac tactgaaact   3240
accgcccctg ttacaacagc tgtcacaacc accgttgtta ccactgaatc ctctacgggt   3300
actaactccg ctggtaagac gacaactagt tacacaacaa agtctgtacc aaccacctat   3360
gtatttgact ttggcaaggg cattctcgat caaagctgcg gcggtgtatt ttcaaacaac   3420
ggctctttgc aagtgcagct gcgggatgca gtcttgatga atgggacagt ggtatacgat   3480
tcaaacggcg cttgggacag tagtgcgctg gaggagtggc tccagcgaca gaaaaaagtt   3540
tccatcgaaa gaatatttga aaatattggg cccagcgccg tgtatccgtc tattttgcct   3600
ggggtcgtga ttgcgtcacc atcgcaaacg catccagact acttctacca atggataagg   3660
gacagcgcgt tgacgataaa cagtattgtc tctcattctg cggacccggc aatagagacg   3720
ttattgcagt acctgaacgt ttcattccac ttgcaaagaa ccaacaacac attgggcgct   3780
ggcattggtt acactaacga tacagtggct ttgggagacc ctaagtggaa cgtcgacaac   3840
acggctttca cggaaccttg gggtcgtcct caaaacgatg gccctgctct tcgaagcatt   3900
gccatcttaa aaatcatcga ctacatcaag caatctggca ctgatctggg ggccaagtac   3960
```

```
ccattccagt ccaccgcaga tatctttgat gatattgtac gttgggacct gaggttcatt   4020
attgaccact ggaattcttc cggatttgat ctatgggagg aagtcaatgg catgcatttc   4080
tttactttac tggtacaact gtctgcagtg gacagatcgc tgtcgtattt taacgcctca   4140
gaacggtcgt ctccctttgt tgaagaattg cgtcagacac gccgggacat ctccaagttt   4200
ttagtggacc ctgcgaatgg gtttatcaac ggcaagtaca attatattgt tgagacaccc   4260
atgattgccg acacattgag atccggactg gacatatcca ctttattagc tgcgaacacc   4320
gtccacgatg cgccatctgc ttcccatctt ccgttcgata tcaatgaccc tgccgtcctg   4380
aacacgttgc accatttgat gttgcacatg cgttcgatat accccatcaa cgatagctcc   4440
aaaaatgcaa cgggtattgc cctgggccgg tatcctgagg acgtatatga tggatatggc   4500
tttggcgagg gaaatccctg ggtcctggcc acgtgtgccg cttcaacaac gctttatcag   4560
ctcatttaca gacacatctc tgagcagcat gacttggttg tcccaatgaa caacgattgt   4620
tcgaacgcat tttggagcga gctggtattc tccaacctca cgactttggg aaatgacgaa   4680
ggctatttga ttttggagtt caatacacct gccttcaatc aaaccataca aaaaatcttc   4740
caactagctg attcattctt ggtcaagctg aaagctcacg tgggaacaga cggggaacta   4800
agtgaacaat ttaacaaata cacagggttt atgcagggtg cccaacacct tacctggtcc   4860
tatacttcat tctgggatgc ctatcaaata agacaagaag ttttacagag tttgtagaca   4920
aaaaaaaata aaagaaaagc gagaagtata cacaagtgta tttcctagat atttacatca   4980
aatatatata tatatactta tttacaaaac tctgatatta taaattagtt agatactatg   5040
tcggaacgtc cagcccaacc acgtttgcag ttcttttcac tttctcatcc tgtgtcaact   5100
tgttgccagg attgtatctg tcgaccagct cctcgtattc tctttggttg tccaagaact   5160
tgatgatgtc caaagcgtgt tcgaatatct cgtcaacgtt ttgtccctgg gccacctttt   5220
tctcc                                                               5225
```

<210> SEQ ID NO 2
<211> LENGTH: 22
<212> TYPE: DNA
<213> ORGANISM: Artificial sequence
<220> FEATURE:
<223> OTHER INFORMATION: Description of sequence: synthetic construct

<400> SEQUENCE: 2

```
cctggctcaa attaaacttt cg                                              22
```

<210> SEQ ID NO 3
<211> LENGTH: 21
<212> TYPE: DNA
<213> ORGANISM: Artificial sequence
<220> FEATURE:
<223> OTHER INFORMATION: Description of sequence: synthetic construct

<400> SEQUENCE: 3

```
accaccaata ggcaatagaa a                                               21
```

<210> SEQ ID NO 4
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 4
caaggcaatc agttaaaaga 20

<210> SEQ ID NO 5
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 5
caactacgac ttctgtcata 20

<210> SEQ ID NO 6
<211> LENGTH: 19
<212> TYPE: DNA
<213> ORGANISM: Artificial sequence
<220> FEATURE:
<223> OTHER INFORMATION: Description of sequence: synthetic construct

<400> SEQUENCE: 6
gatggtgacg caatcacga 19

<210> SEQ ID NO 7
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 7
tggaatgaac agcgccaagt 20

<210> SEQ ID NO 8
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 8
agtgggagaa aaaggtggcc 20

<210> SEQ ID NO 9
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 9
aatgaacagc gccaagtagc 20

<210> SEQ ID NO 10
<211> LENGTH: 21
<212> TYPE: DNA
<213> ORGANISM: Artificial sequence
<220> FEATURE:
<223> OTHER INFORMATION: Description of sequence: synthetic construct

<400> SEQUENCE: 10
ttgaaagcta tgtgcagttg g 21

<210> SEQ ID NO 11
<211> LENGTH: 21
<212> TYPE: DNA
<213> ORGANISM: Artificial sequence
<220> FEATURE:
<223> OTHER INFORMATION: Description of sequence: synthetic construct

<400> SEQUENCE: 11
tgtcccctaa tgtatccctc a 21

<210> SEQ ID NO 12
<211> LENGTH: 22
<212> TYPE: DNA
<213> ORGANISM: Artificial sequence
<220> FEATURE:
<223> OTHER INFORMATION: Description of sequence: synthetic construct

<400> SEQUENCE: 12
aaatcttacc cgtggatcct tt 22

<210> SEQ ID NO 13
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 13
cccaaaattc attcgtagcc 20

<210> SEQ ID NO 14
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 14
tatgcgatgt cccagtacga 20

<210> SEQ ID NO 15
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 15
tgtcaggcat tgcacaaact 20

<210> SEQ ID NO 16
<211> LENGTH: 21
<212> TYPE: DNA
<213> ORGANISM: Artificial sequence
<220> FEATURE:
<223> OTHER INFORMATION: Description of sequence: synthetic construct

<400> SEQUENCE: 16
caattgagaa cccttcaaca a 21

<210> SEQ ID NO 17
<211> LENGTH: 24
<212> TYPE: DNA
<213> ORGANISM: Artificial sequence
<220> FEATURE:
<223> OTHER INFORMATION: Description of sequence: synthetic construct

<400> SEQUENCE: 17
agggcagttt tatttacctt aaca 24

<210> SEQ ID NO 18
<211> LENGTH: 21
<212> TYPE: DNA
<213> ORGANISM: Artificial sequence
<220> FEATURE:
<223> OTHER INFORMATION: Description of sequence: synthetic construct

<400> SEQUENCE: 18
aagtggttgt tgattccgat g 21

<210> SEQ ID NO 19
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 19
tccatgttca accagtccaa 20

<210> SEQ ID NO 20
<211> LENGTH: 18
<212> TYPE: DNA
<213> ORGANISM: Artificial sequence
<220> FEATURE:
<223> OTHER INFORMATION: Description of sequence: synthetic construct

<400> SEQUENCE: 20
ctgtcgctgg agccactc 18

<210> SEQ ID NO 21
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 21
cttgatgaat gggacagtgg 20

<210> SEQ ID NO 22
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 22
gaccgttctg aggcgttaaa 20

<210> SEQ ID NO 23
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 23
tggaattctt ccggatttga 20

<210> SEQ ID NO 24
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 24
ggtttgattg aaggcaggtg 20

<210> SEQ ID NO 25
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 25
agcgagctgg tattctccaa 20

<210> SEQ ID NO 26
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 26
acacgctttg gacatcatca 20

<210> SEQ ID NO 27
<211> LENGTH: 80
<212> TYPE: DNA
<213> ORGANISM: Artificial sequence
<220> FEATURE:
<223> OTHER INFORMATION: Description of sequence: synthetic construct

<400> SEQUENCE: 27
gacggggtat tatgaataaa ggatccacgg gtaagatttg ctgcgctctc ttctagttca 60
agaacggata actcatagac 80

<210> SEQ ID NO 28
<211> LENGTH: 25
<212> TYPE: DNA
<213> ORGANISM: Artificial sequence
<220> FEATURE:
<223> OTHER INFORMATION: Description of sequence: synthetic construct

<400> SEQUENCE: 28
ttccaactgc actagttcct agagg 25

<210> SEQ ID NO 29
<211> LENGTH: 23
<212> TYPE: DNA
<213> ORGANISM: Artificial sequence
<220> FEATURE:
<223> OTHER INFORMATION: Description of sequence: synthetic construct

<400> SEQUENCE: 29
gagctgaatg gagttgaaga tgg 23

<210> SEQ ID NO 30
<211> LENGTH: 29
<212> TYPE: DNA
<213> ORGANISM: Artificial sequence
<220> FEATURE:
<223> OTHER INFORMATION: Description of sequence: synthetic construct

<400> SEQUENCE: 30
gatacttgga atcctggctg gtctgtctc 29

```
<210> SEQ ID NO 31
<211> LENGTH: 32
<212> TYPE: DNA
<213> ORGANISM: Artificial sequence
<220> FEATURE:
<223> OTHER INFORMATION: Description of sequence: synthetic construct

<400> SEQUENCE: 31

aaagggtctt ctgtttcatc acctgtattt gc                              32


<210> SEQ ID NO 32
<211> LENGTH: 29
<212> TYPE: DNA
<213> ORGANISM: Artificial sequence
<220> FEATURE:
<223> OTHER INFORMATION: Description of sequence: synthetic construct

<400> SEQUENCE: 32

cacggatagt ggctttggtg aacaattac                                  29


<210> SEQ ID NO 33
<211> LENGTH: 32
<212> TYPE: DNA
<213> ORGANISM: Artificial sequence
<220> FEATURE:
<223> OTHER INFORMATION: Description of sequence: synthetic construct

<400> SEQUENCE: 33

tatgattatc tggcagcagg aaagaacttg gg                              32


<210> SEQ ID NO 34
<211> LENGTH: 20
<212> TYPE: DNA
<213> ORGANISM: Artificial sequence
<220> FEATURE:
<223> OTHER INFORMATION: Description of sequence: synthetic construct

<400> SEQUENCE: 34

tggctcaaat taaactttcg                                            20
```